United States Patent
Reid

(10) Patent No.: US 9,345,751 B2
(45) Date of Patent: *May 24, 2016

(54) CROTALUS DURISSUS TERRIFICUS VENOM ADMINISTRATION FOR CANCER TREATMENT

(71) Applicant: Celtic Biotech Iowa, Inc., West Des Moines, IA (US)

(72) Inventor: Paul F. Reid, Plantation, FL (US)

(73) Assignee: Celtic Biotech Iowa, Inc., West Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/586,560

(22) Filed: Dec. 30, 2014

(65) Prior Publication Data

US 2015/0110770 A1 Apr. 23, 2015

Related U.S. Application Data

(63) Continuation-in-part of application No. 13/747,409, filed on Jan. 22, 2013, now Pat. No. 8,921,305, which is a continuation of application No. 12/946,792, filed on Nov. 15, 2010, now abandoned.

(60) Provisional application No. 61/261,333, filed on Nov. 14, 2009.

(51) Int. Cl.
*A61K 45/06* (2006.01)
*A61K 38/46* (2006.01)

(52) U.S. Cl.
CPC ............... *A61K 38/465* (2013.01); *A61K 45/06* (2013.01); *C12Y 301/01004* (2013.01)

(58) Field of Classification Search
CPC ............................. A61K 38/465; A61K 45/06
See application file for complete search history.

(56) References Cited

U.S. PATENT DOCUMENTS

| 5,252,213 | A | 10/1993 | Ahmed et al. | |
|---|---|---|---|---|
| 8,921,305 | B2 * | 12/2014 | Reid | 514/1.1 |
| 2007/0148159 | A1 | 6/2007 | Reid et al. | |

OTHER PUBLICATIONS

Andren Sandberg et al., "Annals of Oncology", 1999, pp. s265-s268, vol. suppl 4.
Cura,J. et al., "Phase I and Pharmacokinetics Study of Crotoxin (Cytotoxic PLA2,NSC-624244) in Patients with Advance Cancer", Apr. 2002.
Jenkins et al, "Crotalin—Jenkins and Pendleton", 2009, pp. 1749-1750, Publisher: Jama.
Shattuck et al, "Crotalin, An Improved Method for its Administration", "The Boston Medical and Surgical Journal", 1910, pp. 45-47, vol. 163, No. 2.
Soares Ma et al, "Crotalus durissus terrificus venom as a source of antitumoral agents", "The Journal of Venomous Animals and Toxins including Tropical Diseases", 2010, pp. 480-492, vol. 16, No. 3, Publisher: Jvat td.

* cited by examiner

*Primary Examiner* — Karlheinz R Skowronek
*Assistant Examiner* — Li Lee
(74) *Attorney, Agent, or Firm* — Davis, Brown, Koehn, Shors & Roberts, P.C.

(57) ABSTRACT

A method for treating cancer using an intra-patient dose escalation procedure to deliver dosages of *Crotalus durissus terrificus* venom.

11 Claims, No Drawings

CROTALUS DURISSUS TERRIFICUS VENOM ADMINISTRATION FOR CANCER TREATMENT

CROSS-REFERENCE TO RELATED APPLICATION(S)

This application is a continuation-in-part of U.S. patent application Ser. No. 13/747,409, filed Jan. 22, 2013, which claims the benefit of priority of U.S. patent application Ser. No. 12/946,792, filed Nov. 15, 2010, which claimed the benefit of priority of U.S. Provisional Patent Application No. 61/261,333, filed Nov. 14, 2009 which are each incorporated herein by reference in their entirety.

FIELD OF THE INVENTION

The invention relates to compositions and methods for the treatment of cancer. More specifically, the invention relates to compositions comprising snake venoms and methods for their safe administration for cancer treatment.

BACKGROUND OF THE INVENTION

In 2005, 7.6 million people worldwide died of cancer. Based on projections, cancer deaths will continue to rise with an estimated 9 million people dying from cancer in 2015, and 11.4 million dying in 2030. Each year in the European Union (EU) countries, nearly two million people are diagnosed with cancer and there are over one million deaths from the disease (Cancer Research UK). It is estimated that there are nearly three million people alive in the EU who have received a diagnosis of cancer in the last five years (Cancer Research UK).

There are over 50 drugs used in cancer treatment, but many of these drugs have an average efficacy of about 20% and produce significant side effects. Cancer patients often forego treatment in order to avoid the decreased quality of life associated with side effects such as nausea, vomiting, loss of appetite, weight loss, generalized weakness, and hair loss. In fact, there is a significant demand for drugs that counteract the side-effects of anti-cancer therapy (e.g., Procrit®).

Snake venoms have demonstrated cytotoxic activity on tumour cell lines in vitro, although their anticancer properties in animal models have been studied only in a limited manner. The venoms from cobras contain large amount of basic, non-enzymatic peptides of molecular weight 6.8 kDa, generically called Cardiotoxin, which display cytolytic activity on a broad variety of tumor cells, and to a lesser extent, normal cells. Crotoxin, isolated from the venom of the South American rattlesnake, *Crotalus durissus terrificus*, has proven to have significant and broad acting anti-tumour activity both in-vitro and in-vivo. Its increased affinity for cancer cells is due primarily to the target subunit (A, crotapotin) and cell death is brought about by the B subunit (Crotactine) through the membrane-disrupting enzymatic activity. It has significant potential as a therapeutic agent, but it also has significant neurotoxic activity. Crotoxin, however, induces tolerance to its neurotoxic effects without altering the cytolytic properties, permitting the use of doses above that which would normally be lethal to the host. Mice injected daily with progressively increasing doses of Crotoxin develop tolerance to the lethal action of the toxin. Treated mice tolerated daily doses of Crotoxin 20 to 35 fold higher than the original LD50, without the characteristic signs of toxicity. It has a significantly higher lethal activity toward cancerous cells than normal cells, and this effect has been presumed to be due to the altered make-up of the cell membranes produced by rapidly proliferating cells. The sensitivity of cancer cells to Crotoxin has been associated with their expression of epidermal growth factor, a surface receptor associated with malignancy. Cancer cell lines with the highest sensitivity to Crotoxin include lung, CNS, and melanoma.

Crotoxin has been used in several human safety studies alone and in combination with Cardiotoxin (a combination of Crotoxin and Cardiotoxin in 1:1 ratio is known as VRCTC310) in patients with refractory cancer. Crotoxin, administered by intramuscular injection, was well tolerated when administered alone or in combination with Cardiotoxin, with a maximum tolerable dose (MTD) of 0.21 mg/m$^2$. Upon intramuscular injection Crotoxin achieves maximal circulating levels at 1 hour and is effectively cleared within 24 hours. Several severely ill patients have been reported to respond to treatment with reduced tumor burden, amelioration of pain, and improved quality of life. Given intramuscularly, Crotoxin gives objective clinical responses in doses close to the maximum tolerated dose (MTD). Preclinical animal data suggests that, by using a dose escalation protocol, the administration of very high doses can be achieved without adverse toxicity because the host becomes tolerant to the neurotoxic effects.

To date, subjects treated with Crotoxin have an overall response rate of 43% in a variety of tumour types. When compared to current biologic therapies, Crotoxin appears to be almost twice as active as its nearest competitor. While many other biologic therapies must be combined with conventional treatments and only serve to extend survival by marginal amounts, Crotoxin is a monotherapy, and has demonstrated sufficient activity to results in complete remissions in a relatively high percentage of terminally ill subjects under protocols that have not yet been optimized. It appears that Crotoxin has its highest cytocidal activity against highly malignant cancers, yet the side-effect profile is quite mild in comparison to other forms of chemotherapy or radiotherapy. Side-effects (e.g., diplopia, strabismus, ptosis, peripheral blockade of neuromuscular transmission) do exist, however, and have been reported in dose tolerance studies (Cura, J. et al., "Phase I and Pharmacokinetics Study of Crotoxin (Cytotoxic PLA2, NSC-624244) in Patients with Advanced Cancer," Clinical Cancer Research, Vol. 8, April 2002, p. 1033-1041).

What would be of great benefit, would be the development of methods for optimizing higher dosage levels of Crotoxin while minimizing the neurotoxic side-effects.

BRIEF SUMMARY OF THE INVENTION

The invention relates to Crotoxin compositions for intravenous administration and dosing regimens for administering those compositions to provide a cytotoxic effect on cancer cells and tumors without associated neurotoxic side-effects. Compositions of the invention comprise Crotoxin doses of from about 0.04 to about 0.32 mg/m2 (about 0.0012 to about 0.01 mg/Kg) suitable for intravenous administration using an intra-patient dose escalation procedure. The invention also comprises a method for treating cancer comprising administering to a cancer patient a dosage of from about 0.04 to about 0.32 mg/m2 (0.0012 to 0.01 mg/Kg), the dosage being intravenously administered in an intra-patient dose escalation procedure, the intra-patient dose escalation procedure comprising administering sequentially about 0.04 mg/m2/day for a period of 3-5 days, about 0.12 mg/m2/day for a period of 3-5 days, about 0.16 mg/m2/day for a period of 3-5 days, about 0.20 mg/m2/day for a period of 3-5 days, about 0.24 mg/m2/day for a period of 3-5 days, about 0.28 mg/m2/day for a period of 3-5 days, and about 0.32 mg/m2/day for a period of 3-5 days. In some aspects, the procedure may further comprise a two-day non-treatment period between each 3- to 5-day treatment period. In some aspects, the procedure may also comprise administration by saline drip over a two-hour period.

The invention also relates to methods of use of Crotoxin comprising intra-patient dose escalation of Crotoxin injections for the treatment of pain and/or for the treatment of neurologic and/or neuromuscular disorders. Pain may be associated with cancer, with arthritis, with multiple sclerosis, or any of a variety of sources of pain. In one aspect, the intra-patient dose escalation protocol is effective for the alleviation of pain associated with pancreatic cancer.

The invention also relates to methods of use of Crotoxin injections provided in an intra-patient dose escalation protocol in conjunction with the administration of aspirin (acetylsalicylic acid) for the alleviation of pain.

DETAILED DESCRIPTION

The inventors have developed an intra-patient dose escalation procedure for intravenous administration of Crotoxin for the treatment of cancer. The method may also be used for administration of Crotoxin for the treatment of pain and for the treatment of diseases associated with autoimmunity and inflammation. In the procedure, Crotoxin doses of from about 0.04 to about 0.32 mg/m2 (0.0012 to 0.01 mg/Kg) are administered daily by intravenous administration over a 2-hour period by saline drip. The definition of DLT (dose-limiting toxicity) in the context of this procedure is described as inability of a patient to tolerate dose escalation twice. Should Crotoxin-related toxicity occur, as evidenced by neurological side-effects resulting from peripheral blockade of neuromuscular transmission, a patient is given the previous dose for another cycle (3-5 days), and upon completion of the repeated cycle, 2nd dose escalation is attempted. If the patient responds with Crotoxin-related toxicity after the 2nd dose escalation attempt, the escalation is abandoned for this patient and the dose to which escalation was made is assessed as DLT for this patient. The patient is allowed to remain on the highest tolerated dose for another 4 weeks, subject to clinical assessment from the treating physician. After 4 weeks, tumor assessment is performed to assess potential efficacy of the dosage. Example dosing regimens are shown in Tables 1 and 2.

Briefly the method for treating cancer comprises administering to a cancer patient at least one Crotoxin dosage of from about 0.04 to about 0.32 mg/m$^2$, the dosage being intravenously administered in an intra-patient dose escalation procedure, the intra-patient dose escalation procedure comprising consecutive administration of about 0.04 mg/m$^2$/day for a 3-5 day treatment period, about 0.12 mg/m$^2$/day for a 3-5 day treatment period, about 0.16 mg/m$^2$/day for a 3-5 day treatment period, about 0.20 m g/m$^2$/day for a 3-5 day treatment period, about 0.24 mg/m$^2$/day for a 3-5 day treatment period, 0.28 m g/m$^2$/day for a 3-5 day treatment period, and 0.32 mg/m$^2$/day for a 3-5 day treatment period, wherein each successive dose escalation is conditioned upon the absence of dose-limiting toxicity from the previous dose. The intra-patient dose escalation procedure may include a two-day non-treatment period between each treatment period. For example, treatment may be performed during weekdays (i.e., Monday through Friday), with a break from treatment on the weekend.

The dosage provided in the method may be, for example, administered intravenously, such as by saline drip. In one aspect, administration may be performed by intravenous saline drip over about a two hour period.

The invention also provides a method for treating pain in a patient comprising administering to the patient at least one Crotoxin dosage of from about 0.04 to about 0.32 mg/m$^2$, the dosage being intravenously administered in an intra-patient dose escalation procedure, the intra-patient dose escalation procedure comprising consecutive administration of about 0.04 mg/m$^2$/day for a 3-5 day treatment period, about 0.12 mg/m$^2$/day for a 3-5 day treatment period, about 0.16 mg/m$^2$/day for a 3-5 day treatment period, about 0.20 m g/m$^2$/day for a 3-5 day treatment period, about 0.24 mg/m$^2$/day for a 3-5 day treatment period, 0.28 mg/m$^2$/day for a 3-5 day treatment period, and 0.32 mg/m$^2$/day for a 3-5 day treatment period, wherein each successive dose escalation is conditioned upon the absence of dose-limiting toxicity from the previous dose. In various aspects, the pain may be associated with cancer, arthritis, multiple sclerosis, and/or other disease conditions which are associated with pain. In certain aspects, the pain may be associated with pancreatic cancer, which has been described to be a particularly painful condition, with pain at later stages of the disease being refractory to many forms of pain relief.

For the treatment of pain, an intra-patient dose escalation protocol may comprise intravenous administration as provided in Table 1 and/or Table 2, or may comprise Crotoxin injection with or without the administration of aspirin, in a dosing regimen comprising a minimal dose of about 0.05 cc or about 0.1 cc given for a period of 5 days, followed by incremental increases in dosage administered for similar periods of time (e.g., 3-5 days). Diphenhydramine (e.g., Benadryl®) may also be pre-administered or co-administered to minimize a reaction to the Crotoxin.

TABLE 1

| Dosing Regimen #1 | | | |
|---|---|---|---|
| Dose Level | CROTOXIN Daily Dose | Days (starting Monday), no treatment on weekends | Duration In days |
| 1 | 0.04 mg/m$^2$/day | 1-5 | 5 |
| 2 | 0.08 mg/m$^2$/day | 8-12 | 5 |
| 3 | 0.12 mg/m$^2$/day | 15-19 | 5 |
| 4 | 0.16 mg/m$^2$/day | 22-26 | 5 |
| 5 | 0.20 mg/m$^2$/day | 29-33 | 5 |
| 6 | 0.24 mg/m$^2$/day | 36-40 | 5 |
| 7 | 0.28 mg/m$^2$/day | 43-47 | 5 |
| 8 | 0.32 mg/m$^2$/day | 50-54 | 5 |

TABLE 2

| Dosing Regimen #2 | | | |
|---|---|---|---|
| Dose Level | CROTOXIN Daily Dose | Days (starting Monday), no treatment on weekends | Duration In days |
| 1 | 0.04 mg/m$^2$/day | 1-3 | 3 |
| 2 | 0.08 mg/m$^2$/day | 4-5, 8-10 | 5 |
| 3 | 0.12 mg/m$^2$/day | 11-12, 15 | 3 |
| 4 | 0.16 mg/m$^2$/day | 16-18 | 3 |
| 5 | 0.20 mg/m$^2$/day | 19, 22-24 | 4 |
| 6 | 0.24 mg/m$^2$/day | 25-26, 29 | 3 |
| 7 | 0.28 mg/m$^2$/day | 30-32 | 3 |
| 8 | 0.32 mg/m$^2$/day | 33, 36-37 | 3 |

According to further embodiments, Crotoxin is administered in the form of whole venom. In certain embodiments, the venom is from *Crotalus durissus terrificus* (CDTV). *Crotalus durissus terrificus* consists of equivalent Crotoxin and Crotamine which are both reported to have antitumor activity and according to certain embodiments, this combination has synergistic effects on the reduction of cancer. *Crotalus durissus terrificus* is known to cause a myriad of toxic effects being particularly injurious to the kidneys especially by intravenous administration. The parenteral administration of crotamine is particularly problematic due to its localized myonecrotic effects, causing significant pain greater even than that affected by crotoxin by the same route. However, these toxic effects of CDTV can be mitigated by administration of CDTV according to dose ramping protocol disclosed herein. Other *Crotalus* species may have a different venom composition, wherein the Crotamine fraction may be diminished or lost, and therefore may not have the desired effect. However, any *Crotalus* species with substantial Crotamine and Crotoxin components may be suitable for the disclosed methods.

According to certain embodiments, a standard dose of antihistamine (particularly in humans) is administered upon the initiation of treatment. In certain embodiments, CDTV is administered about thirty minutes after the antihistamine. According to certain embodiments, CDTV is administered via intratumor or subcutaneous administration when intravenous administration is not feasible.

For humans, intravenous administration is preferred in order to avoid the myonecrotic effects of the venom. In certain embodiments, an intravenous port is used which allows for repeated injection of CDTV. In further embodiments, lower doses of the CDTV require the addition of saline in order to ensure CDTV enters the blood stream and not stand in the port.

According to certain embodiments, a starting does is selected which is about 0.04 mg or 0.1 mL of CDTV. A dose increase of about 0.1 mL is administered every 3 days up to a dose of 0.4 mg or 1.0 mL. Thereafter the dose is increased by 0.1 mL about every 5 days until a dose of 0.8 mg (2 mL) is reached. According to certain embodiments, once the maximum dose of 0.8 mg is reached, that dose is administered daily for 90 days. In further embodiments, higher doses may be reached by extending the escalation protocol, either increasing the volume and prolonging the duration of the injection or increasing the frequency of injection in a way that avoids the bolus effect of administration. According to certain embodiments, the dose escalation procedure used for CDTV is the same as that described herein for crotoxin.

Thereafter, depending on the response rate, CDTV may be administered daily or every other day for another 90 days. Treatment may be continued as needed until tumor clearance is attained or intermittent treatment, dosing 2-3 times a week, can be used to maintain the disease under control. If treatment is suspended for 3-4 weeks the dose ramping protocol is repeated to avoid toxic effects along with the use of antihistamines to suppress allergic reactions.

In certain aspects, disclosed is a method for treating cancer comprising: administering to a cancer patient at least one *Crotalus durissus terrificus* venom dosage of from about 0.04 to about 0.8 mg, the dosage being intravenously administered in an intra-patient dose escalation procedure, the intra-patient dose escalation procedure comprising consecutive administration of: about 0.04 mg/day for a 3-5 day treatment period; about 0.08 mg/day for a 3-5 day treatment period; about 0.12 mg/day for a 3-5 day treatment period; about 0.16 mg/day for a 3-5 day treatment period; about 0.2 mg/day for a 3-5 day treatment period; about 0.24 mg/day for a 3-5 day treatment period; about 0.28 mg/day for a 3-5 day treatment period; about 0.32 mg/day for a 3-5 day treatment period; about 0.36 mg/day for a 3-5 day treatment period; about 0.4 mg/day for a 3-5 day treatment period; about 0.44 mg/day for a 3-5 day treatment period; about 0.48 mg/day for a 3-5 day treatment period; about 0.52 mg/day for a 3-5 day treatment period; about 0.56 mg/day for a 3-5 day treatment period; about 0.6 mg/day for a 3-5 day treatment period; about 0.64 mg/day for a 3-5 day treatment period; about 0.68 mg/day for a 3-5 day treatment period; about 0.72 mg/day for a 3-5 day treatment period; about 0.76 mg/day for a 3-5 day treatment period; and about 0.8 mg/day for a 3-5 day treatment period; wherein each dose is co-administered with an antihistamine; and wherein each successive dose escalation is conditioned upon the absence of dose-limiting toxicity from the previous dose.

According to further aspects, the intra-patient dose escalation procedure further comprises a two-day non-treatment period between each treatment period. According to still further aspects, the dosage is intravenously administered by saline drip. According to yet further aspects, the antihistamine is administered intravenously. According to yet further aspects, the antihistamine is administered orally. According to still further aspects, the administration of 0.8 mg/day treatment period is continued for about 90 days. In further aspects, the maximal dose is administered until the cancer patient's tumor has substantially reduced in size. In yet further aspects, the method further comprises administering a dose of about 0.2 mg every other day to prevent tumor recurrence.

The invention may be further described by means of the following non-limiting examples.

EXAMPLES

Multi-Patient 2-Cohort Study

Individuals selected for the study are adult patients with histologically confirmed advanced solid tumors who have progressed despite standard therapy, or for whom no standard therapy exists; have an ambulatory PS (ECOG 0-1); have tumour evaluation made within 28 days before study drug administration (patients with non-measurable lesions according to the RECIST guidelines not previously irradiated are allowed to enter the trial); have completed radiotherapy or chemotherapy or any other anticancer therapy (including experimental therapy) more than 4 weeks prior to enrollment into the trial and must have recovered from all acute side effects of these treatments; have a life expectancy greater than 3 months; have an age between 18 and 75 years; have normal marrow function with normal haematological parameters (Hb≥10 g/dl, WBC≥4.0×1Q91L, neutrophil count≥2.0×1Q9/L and platelets≥100×1Q9/L); have no medically significant impairment of cardiac or respiratory functions; have adequate hepatic function with total bilirubin≥1.5×N and transaminases≥2.5×N (≥5×N in case of liver metastasis); have no history of prior severe allergic reactions to venoms; have creatinine clearance 50 ml/min.

Additionally, patients must already be on stable doses of any drugs which may affect hepatic drug metabolism or renal drug excretion (e.g., non-steroidal anti-inflammatory drugs, barbiturates, narcotic analgesics, probenecid), they should not be pregnant or planning to become pregnant, should not be known to have brain metastases or leptomeningeal involvement (CT-scan or MRI is not required to rule this out unless there is clinical suspicion of central nervous system involvement), should not have pleural effusion/ascites, cystic lesions or bone metastases, should not be receiving any other experimental or anti-cancer therapy within 30 days before first study drug administration (except antalgic radiotherapy and hormonotherapy), should not have a history of other malignancies (except for patients with a cancer free interval of greater than or equal to 5 years after treatment completion or patients with prior history of adequately treated basal cell carcinoma of the skin or carcinoma in situ of the cervix), should not have had recent major surgery (within 21 days) should not have a recent history of weight loss greater than 10% of current body weight, should not have serious intermittent medical illnesses which would interfere with the ability of the patient to carry out the treatment program, should not be on chronic steroid medication (greater than 20 mg/day), and should not have primary or paraneoplastic myasthenia gravis.

Crotoxin doses of about 0.04 to 0.32 mg/m$^2$ (0.0012 to 0.01 mg/Kg) are administered using an intra-patient dose escalation procedure. The definition of DLT (dose-limiting toxicity) in the context of this study is described as inability of dose escalation twice. Should Crotoxin-related toxicity occur, the patient is given the previous dose for another cycle (5 days) upon which 2nd dose escalation is attempted. If the patient responds with drug treatment related Crotoxin-related toxicity after the 2nd dose escalation attempt, the escalation is abandoned for this patient and the dose to which escalation was made is assessed as DLT for this patient. The patient is offered to remain on the highest tolerated dose for another 4 weeks, subject to clinical assessment from the treating physician. After 4 weeks, tumor assessment is performed to assess potential efficacy of the tested compound.

Determination of general MTD may be done as follows: first, a patient is treated up to a 0.32 mg/m2 or a lower tolerated dose. This dose is called the i$^{th}$ target ceiling dose (TCDi). Next, two patients will be treated up to the TCDi. If no Crotoxin-related toxicity (dose-limiting toxicity, DLT) is encountered at the TCDi, then the TCDi is the MTD. If two or more DLT are encountered, then 3 new patients are included to receive the next lower dose (TCDi-1), etc. If one DLT is encountered, then 3 more patients are added to receive dosages up to the TCDi. If no DLT is encountered among those 3 new patients, then the TCDi is MTD. If one or more DLT is encountered among those 3 new patients, then 3 new patients are included up to TCDi-1, etc.

Crotoxin is administered daily by intravenous administration over a 2-hour period by saline drip. Each patient will receive Ranitidine 50 mg (antiemetic) and Polaramine® 10 mg I.V. 10 mg (antihistamine) intravenously prior to treatment to minimize the potential for anaphylaxis.

Patients are treated as out-patients, attending the clinic daily for treatment, monitored at the clinic for the duration of the infusion (2 hours), and observed for 30 minutes following the infusion of the drug. If adverse events are to occur (anaphylaxis or neurotoxicity), they are expected to manifest themselves during the administration of the drug allowing interruption of treatment (stopping of the infusion) as circulating levels of the drug will rapidly fall once administration has ceased. The procedure to suppress the potential for anaphylaxis is followed in a standard protocol employed for any agent that can induce hypersensitivity reaction (e.g., such procedures are employed when administering Radio Contrast Media and monoclonal antibody therapies such as trastuzumab or cetuximab).

Crotoxin Administration Alleviates Pain Related to Pancreatic Cancer and Multiple Sclerosis A female patient with both pancreatic cancer and multiple sclerosis experienced such pain that it was not alleviated by medications such as hydromorphone and/or fentanyl. She began a dose escalation protocol comprising injectable Crotoxin starting at 0.01 cc. A dose of 0.1 cc contains 40 micrograms Crotoxin or about 0.6 micrograms/kilogram. She has been maintained at the 0.1 cc dose and reports being pain free and able to move muscles and joints without experiencing pain. Of even more significance, she reports experiencing no pancreatic pain. The decrease in pain was of such magnitude that the patient experienced it as a sense of euphoria.

*Crotalus durissus terrificus* Administration Reduces Cancer and has Low Toxicity Example 1

Using the dose ramping protocol a 11 year old female spaniel mix diagnosed with one benign and one malignant mast cell tumor, a common cancer in dogs, was treated intratumorly and subcutaneously with *Crotalus durissus terrificus* venom in a solution of 0.4 mg/mL in saline. The dog had previously been treated with Crotoxin without significant benefit. The initial dosing phase included the oral administration of diphenhydramine (25 mg) to reduce the potential for allergic responses. The malignant tumor, located on the mammary gland, had a diameter of 7 cm while the benign tumor, of similar size, was located on the rib cage. Over the course of 9 months a maximum dose of 0.4 mg per dose was employed and the malignant tumor was cleared. There was little change in the benign mass. No toxic or allergic responses were observed. To prevent the recurrence, the animal was treated every other day with 0.5 ml (0.2 mg) of venom.

Example 2

Using the dose ramping protocol disclosed herein, a 10 year old male German shepherd and Rottweiler mix with a benign mast cell tumor, common in dogs, was treated intratumorly and subcutaneously with *Crotalus durissus terrificus* venom in a solution of 0.4 mg/mL in saline. The initial dosing phase did not include the oral administration of diphenhydramine. The tumor, located on the rib cage, had a diameter of 9 cm. Over the course of 6 months a maximum dose of 0.4 mg per dose was employed and the tumor has remained static. No toxic or allergic responses were observed. To prevent further exacerbation the animal is treated every other day with 0.75 ml (0.3 mg) of venom.

Example 3

Instantly disclosed dose ramping protocol was administered to a 60 year old male human, diagnosed with colon cancer consisting of two small masses in the large intestine. The subject was treated intravenously with *Crotalus durissus terrificus* venom in a solution of 0.4 mg/mL in saline Surgical resection of the intestine was rejected, no other treatment protocols were undertaken. The initial dosing phase included the oral administration of cimetidine (Tagamet®). Over the course of 18 months, a starting dose of 0.04 mg and a maximum dose of 0.8 mg (2 mL) per dose was employed. A positron emission tomography (PET) scan indicated the larger and more malignant tumor was cleared at 6 months. A second PET scan at 16 months revealed that all tumor were cleared. No toxic or allergic responses were observed.

Example 4

Using the dose ramping protocol a 17 year old male, diagnosed with an astrocytoma unresponsive to surgical removal, was treated intravenously with *Crotalus durissus terrificus* venom in a solution of 0.4 mg/mL in saline. The initial dosing phase included the oral administration of diphenhydramine (Benedryl®). Over the course of 3 months a maximum dose of 0.8 mg (2 mL) per dose was employed. Data on tumor responsiveness has not been attained however no toxic or allergic responses have been observed.

Although the present invention has been described with reference to preferred embodiments, persons skilled in the art will recognize that changes may be made in form and detail without departing from the spirit and scope of the invention.

What is claimed is:

1. A method for treating cancer comprising:
administering to a cancer patient at least one *Crotalus durissus terrificus* venom dosage of from about 0.04 to about 0.8 mg, the dosage being intravenously administered in an intra-patient dose escalation procedure, the intra-patient dose escalation procedure comprising consecutive administration of:
about 0.04 mg/day for a 3-5 day treatment period;
about 0.08 mg/day for a 3-5 day treatment period;
about 0.12 mg/day for a 3-5 day treatment period;
about 0.16 mg/day for a 3-5 day treatment period;
about 0.2 mg/day for a 3-5 day treatment period;
about 0.24 mg/day for a 3-5 day treatment period;
about 0.28 mg/day for a 3-5 day treatment period;
about 0.32 mg/day for a 3-5 day treatment period;
about 0.36 mg/day for a 3-5 day treatment period;
about 0.4 mg/day for a 3-5 day treatment period;
about 0.44 mg/day for a 3-5 day treatment period;
about 0.48 mg/day for a 3-5 day treatment period;
about 0.52 mg/day for a 3-5 day treatment period;
about 0.56 mg/day for a 3-5 day treatment period;
about 0.6 mg/day for a 3-5 day treatment period;
about 0.64 mg/day for a 3-5 day treatment period;
about 0.68 mg/day for a 3-5 day treatment period;
about 0.72 mg/day for a 3-5 day treatment period;
about 0.76 mg/day for a 3-5 day treatment period;
and about 0.8 mg/day for a 3-5 day treatment period;
and wherein each successive dose escalation is conditioned upon the absence of dose-limiting toxicity from the previous dose.

2. The method of claim 1 wherein each dose is co-administered with an antihistamine.

3. The method of claim 1 wherein the intra-patient dose escalation procedure further comprises a two-day non-treatment period between each treatment period.

4. The method of claim 1 wherein the dosage is intravenously administered by saline drip.

5. The method of claim 2 wherein the antihistamine is administered intravenously.

6. The method of claim 2 wherein the antihistamine is administered orally.

7. The method of claim 1 wherein the administration of 0.8 mg/day treatment period is continued for about 90 days.

8. The method of claim 1 wherein the cancer patient has a tumor and wherein the maximal dose is administered until the cancer patient's tumor has reduced in size, relative to the size of the tumor at the beginning of treatment.

9. The method of claim 8 further comprising administering a dose of about 0.2 mg every other day to maintain the reduced tumor size.

10. The method of claim 1, wherein the cancer patient is a non-human mammal.

11. The method of claim 10, wherein the non-human mammal is a canine.

* * * * *